(12) United States Patent
Gerges et al.

(10) Patent No.: US 10,743,982 B2
(45) Date of Patent: Aug. 18, 2020

(54) BIODEGRADABLE MEDICAL DEVICE FOR BREAST RECONSTRUCTION AND/OR AUGMENTATION

(71) Applicant: TENSIVE SRL, Milan (IT)

(72) Inventors: Irini Gerges, Milan (IT); Federico Martello, Milan (IT); Margherita Tamplenizza, Alessandra (IT); Alessandro Tocchio, Woodside, CA (US)

(73) Assignee: TENSIVE SRL, Milan (IT)

( * ) Notice: Subject to any disclaimer, the term of this patent is extended or adjusted under 35 U.S.C. 154(b) by 203 days.

(21) Appl. No.: 15/756,888

(22) PCT Filed: Sep. 1, 2016

(86) PCT No.: PCT/IB2016/055238
§ 371 (c)(1),
(2) Date: Mar. 1, 2018

(87) PCT Pub. No.: WO2017/037649
PCT Pub. Date: Mar. 9, 2017

(65) Prior Publication Data

US 2018/0250122 A1 Sep. 6, 2018
US 2019/0336271 A2 Nov. 7, 2019

(30) Foreign Application Priority Data

Sep. 2, 2015 (IT) .................. 102015000047951

(51) Int. Cl.
*A61F 2/12* (2006.01)
*A61L 27/18* (2006.01)
(Continued)

(52) U.S. Cl.
CPC ............... *A61F 2/12* (2013.01); *A61L 27/18* (2013.01); *A61L 27/56* (2013.01); *A61L 27/58* (2013.01);
(Continued)

(58) Field of Classification Search
CPC .................................. A61F 22/12; A61F 2/12
(Continued)

(56) References Cited

U.S. PATENT DOCUMENTS 10,323,116 B2 * 6/2019 Svenson ............ C08G 18/4883
2005/0043816 A1 * 2/2005 Datta ..................... A61L 27/18
623/23.61
(Continued)

FOREIGN PATENT DOCUMENTS

WO 2009097347 A1 6/2009

OTHER PUBLICATIONS

PCT/IB2016/055238, Written Opinion and International Search Report, Nov. 23, 2016, 8 pages.

*Primary Examiner* — Suzette J Gherbi
(74) *Attorney, Agent, or Firm* — Abelman, Frayne and Schwab (57) ABSTRACT

An implantable biodegradable medical device arranged for breast reconstruction and/or augmentation, made of an interconnected porous structured polymeric matrix and belonging to the family of poly(urea urethane)s.
The porous structured polymeric matrix of the medical device comprises a plurality of three dimensional channels, drilled by means of heated tools, three-dimensionally propagating through the polymeric matrix ad interconnected with the porous structure of the polymeric matrix.
The polymeric matrix comprises high to-medium molecular weight hydrophobic biodegradable amorphous soft segments polyols, having average molecular weight comprised
(Continued)

between 20'000 and 60'000 Da,—hydrophilic polyalkoxide polyols, of average molecular weight comprised between 2'000 and 15'000 Da, and low molecular weight polyisocyanates and polyols, whose average molecular weights range between 15 and 200 Da.

16 Claims, 7 Drawing Sheets

(51) Int. Cl.
| | |
|---|---|
| *A61L 27/56* | (2006.01) |
| *A61L 27/58* | (2006.01) |
| *C08G 18/32* | (2006.01) |
| *C08G 18/42* | (2006.01) |
| *C08G 18/48* | (2006.01) |
| *C08G 18/73* | (2006.01) |
| *C08G 18/75* | (2006.01) |
| *B29C 39/00* | (2006.01) |
| *B29K 75/00* | (2006.01) |
| *B29K 105/04* | (2006.01) |
| *B29L 31/00* | (2006.01) |

(52) U.S. Cl.
CPC ......... *C08G 18/3206* (2013.01); *C08G 18/42* (2013.01); *C08G 18/48* (2013.01); *C08G 18/73* (2013.01); *C08G 18/755* (2013.01); *A61F 2210/0004* (2013.01); *A61F 2230/0069* (2013.01); *A61F 2230/0071* (2013.01); *A61F 2240/002* (2013.01); *A61L 2430/04* (2013.01); *B29C 39/003* (2013.01); *B29K 2075/00* (2013.01); *B29K 2105/04* (2013.01); *B29K 2995/006* (2013.01); *B29K 2995/0088* (2013.01); *B29L 2031/7532* (2013.01)

(58) Field of Classification Search
USPC ......................................................... 623/7–8
See application file for complete search history.

(56) References Cited

U.S. PATENT DOCUMENTS

| | | |
|---|---|---|
| 2008/0262613 A1 | 10/2008 | Gogolewski |
| 2010/0114312 A1 | 6/2010 | Glicksman |
| 2011/0029077 A1 | 2/2011 | Choi |
| 2012/0158134 A1* | 6/2012 | Codori-Hurff ............ A61F 2/12 623/8 |
| 2012/0239161 A1* | 9/2012 | Datta ..................... A61L 27/18 623/23.72 |
| 2015/0182670 A1* | 7/2015 | Rizk ..................... A61L 31/06 514/772.3 |
| 2018/0250122 A1* | 9/2018 | Gerges ..................... A61F 2/12 |
| 2019/0192727 A1* | 6/2019 | Basore ................. A61L 24/001 |

* cited by examiner

BIODEGRADABLE MEDICAL DEVICE FOR BREAST RECONSTRUCTION AND/OR AUGMENTATION

RELATED APPLICATIONS

This application is a United States national phase application under 35 USC § 371 of PCT/IB2016/055238 filed on Sep. 1, 2016, and claims the benefit under 35 USC § 119 of Italian patent application number 102015000047951 filed Sep. 2, 2015, the disclosures of which are both incorporated herein by reference in their entireties.

TECHNICAL FIELD

Present invention relates, in general, to the field of regenerative medicine for soft tissues reconstruction.
More specifically, the invention relates to an implantable biodegradable or bioresorbable medical device for breast reconstruction and/or augmentation.

BACKGROUND ART

In the field of regenerative medicine, soft tissues reconstruction is generally known and, in particular, breast reconstruction is known.

Breast reconstruction aims to restore a breast to near normal shape, appearance and size, following mastectomy, quadrantectomy or lumpectomy, through several plastic surgeries.

The high incidence of breast cancer is a prominent driver for the breast reconstruction market. Currently, there are over 10 million breast cancer survivors worldwide.

These women typically undergo mastectomies (total breast removal), quadrantectomies or lumpectomies (only the tumor and part of surrounding tissue is removed) as part of their treatment.

The loss of a breast may have a profound impact on women's quality of life and breast reconstruction is routinely offered (to 60% of women underwent mastectomy) to improve outcomes.

The known reconstructive options are so far limited to whole breast saline or silicone non-resorbable implants.

Due to the fact that it is difficult to treat a wide variety of soft tissue deficits resulting from quadrantectomy or lumpectomy procedures in patients, according to the known prior art there are very few reconstructive options for those patients.

Another constraint of the known non-resorbable implants is the perception that cancer might not be detected if the area is covered by such non-resorbable implants, which could hide suspicious lesions or rupture in the implants during screening.

Besides implant-based reconstruction/augmentation, fat auto-transplantation represents the only known viable alternative procedure currently available in the field. According to this procedure, the fat is removed by liposuction from different parts of the patient's body and then injected into the breast.

Transplantation of autologous adipose tissue fraction ("free-fat grafting") rarely achieves sufficient tissue augmentation because of delayed neovascularization of the grafted adipose tissue, with consequent cell necrosis, and graft volume shrinkage, losing up to 60% of its volume after transplantation. This is due to the fact that fat cells require immediate nutrition from the bloodstream in order to survive.

Attempts aiming to obtain implantable adipose tissue substitutes, through the combination of cells, growth factors and three dimensional polymer matrixes, called "scaffold", are also known in the art.

However the substitutes so far obtained are dimensionally limited, due to the lack of vascularization and efficient transportation of nutrients and oxygen to inner core of the scaffold.

Regarding to the porous polymeric matrixes used in the art to make scaffold, the most investigated for adipose tissue regeneration are mainly natural origin polymers. Limitations of the employment of natural polymers in the development of medical devices which aim to regenerate adipose tissue are mainly related to their elevated costs, variable quality from batch-to-batch, expensive isolation processes and the possibility to cause immune response, due to endotoxins belonging to their allogenic or xenogenic origin.

Due to the limitations of natural polymers, synthetic polymers are becoming a more valid alternative in comparison to natural polymers, thanks to the low cost and the possibility to tune their physico-chemical properties, in order to match the target application.

Currently, the most common limits against the employment of porous synthetic polymers in adipose tissue regeneration are related to their physico-chemical properties, such as mechanical properties, hydrophilic character, and degradation kinetics, which do not exactly match all the requirements of adipose tissue ingrowth in vivo.

Among synthetic polymeric materials used in implantable medical device, polyurethane-based polymers are known.

According to prior art, the employment of polyurethane forms in implantable medical device for breast surgery, is so far limited to the enhancement of biocompatibility of silicon-based breast prostheses, through surface coating of the latter by thin layers of polyurethane foam. For example, according to WO9006094, a polyurethane coating of a silicon-based prosthesis is uniformly mixed to collagen.

Attempts aimed to employ polyurethane-based porous matrices in tissue engineering and regenerative medicine are also known in the art.

Such a class of synthetic biomaterials are mostly studied and developed for bone tissue regeneration, thanks to their high stiffness and creep resistance, in addition to the possibility to introduce inorganic mineral fillers, similar to those abundantly present in bone tissue, in order to increase their osteoconductivity.

According to US20050013793 and US20130295081, it is possible to obtain biodegradable rigid poly(urethane ester) foams for bone tissue engineering, via copolymerization of biodegradable low-molecular weight hard and soft segments (average molecular weight from 200 to 900 Da) into the polymeric structure, by applying a "pre-polymer" casting strategy.

According to CA2574933 A1, biocompatible and biodegradable segmented polyurethanes of controlled hydrophilic to hydrophobic ratio are obtained due to copolymerisation of biodegradable polyols (average molecular weight from 100 to 20,000 Da), and polyisocyanates (average molecular weight from 18 to 1000 Da), according to a "quasi-pre-polymer" casting strategy.

The cross-linked segmented polyurethane foams, synthesized according to CA2574933 A1, are characterized by compressive elastic moduli comprised between 7 and 72 MPa, resulting in rigid foams and more suitable for bone repair but not for soft tissue regeneration.

Applicant has noticed that cross-linked polyurethane foams disclosed in the above documents do not have the mechanical properties required for soft tissue regeneration; in particular, according to the above prior art documents, is not possible to obtain soft foams, having compressive moduli comprised between 5 to 700 kPa.

With regards to scaffold used in adipose tissue substitutes, the possibility to promote angiogenesis and to enhance cell viability, both in vivo and in vitro, through channelization of porous matrices, is known ("Tamplenizza et al. Mol Imaging. 2015 May 1; 14:11-21", "Zhang et al. Biomaterials. July 2015; 68-77, Tocchio et al, Biomaterials. March 2015, 45; 124-131" and WO20121645512).

According to prior art, developments of channeled porous scaffolds can take place by several techniques, as for example:
1) sacrificial templating, as disclosed in "Tocchio et al. Biomaterials. March 2015, 45; 124-131" and in WO20121645512 A1;
2) injection molding, as disclosed in "Zhi-xiang, et al. Chinese Journal of Polymer Science. 2014, 32(7); 864-870";
3) phase separation, as disclosed in US2006069435 A1;
4) Selective Laser Sintering (SLS), as disclosed in "Patri K. Venuvinod, Weiyin Ma. Selective Laser Sintering (SLS). Rapid Prototyping, 2004, pp 245-277";
5) additive manufacturing techniques, as disclosed in "Melchels F P W, Domingos M A N, Klein T J, Malda J, Bartolo P J and Hutmacher D W. Additive manufacturing of tissues and organs Prog. Polym. Sci. 37 (2012) 1079-1104"; and
6) drilling, as disclosed in US20080261306 A1.

However, the Applicant has found that all these techniques present different limitations when used for the fabrication of channelized porous scaffolds at industrial scale; these limitation are related to scalability, cost, complexity and compatibility with different biomaterials.

In particular, for sacrificial methods 1) the limitations are related to:
i) the necessity to dissolve away the sacrificial templates from the porous scaffolds after solidification (this process takes place mainly by extensive exposure of the porous polymer to several washing cycles, which may alter the overall physico-chemical properties of the polymer, in addition to the high impact of these washing cycles on production coasts);
ii) difficulties to obtain homogeneous pores around the sacrificial templates, especially when the porous scaffold is obtained by foaming;
iii) impossibility to obtain complex three-dimensional sacrificial template networks, when the template networks are produced by injection molding;
iv) difficulties to obtain three-dimensional sacrificial template networks by 3D printing of thermo-plastic polymers, due to the collapse of the filaments during polymer deposition (to this purpose, it would be necessary to assemble several 2D templates, which rendered the process more complicated and less versatile).

With regard to the injection molding 2), despite being the most adopted process for polymers shaping on industrial scale, it is not suitable for the production of complex three-dimensional channels inside soft polymeric foams, due to the inevitable alteration of the porous structure and the formation of this non-porous films in proximities of the mold walls, which are usually called "skin".

For phase separation methods 3), the limitations are related to the prolonged passages to eliminate solvent/non-solvents, which may alter the scaffolds physico-chemical properties in addition to the lack of versatility of the process.

For Selective Laser Sintering method 4), the main disadvantages consist in:
i) the high power consumption, and consequently the elevated process cost;
ii) necessity to control temperatures within 2° C. for the three stages of the method, i.e. preheating, melting and storing.

As for additive manufacturing techniques 5), the main drawbacks consist in
i) high manufacturing costs
ii) limited choice of materials usable
iii) limited scalability due a general slowness of the production process compared with other techniques.

As for common drilling techniques 6), they cannot be applied to soft and flexible porous polymeric matrixes, since the only use of a mandrel to perforate the porous matrix is not able to create stable channels or cavities, due to deformation and the collapse of the latter, under the effect of the local compression force exerted by the mandrel during perforation.

With regard to the common sacrificial and drilling techniques 6) and, in particular, to prior art document US20080261306 A1, a mandrel-based molding technique is used to create rectilinear channels inside a scaffold, in order to improve perfusion for in vitro applications.

However, this technique cannot be applied to most porous biomaterials, since the cells are grown directly on the mandrel before the formation of the solid gel matrix constituting the scaffold and most porous biomaterial synthetic processes do not allow the presence of cells during the curing phase.

In an alternative example disclosed in the same document, the cells are grown in the channel after the removal of the mandrel to form a parent vessel.

In this case, the formation of a parent vessel needs a channel having a continuous wall, without pores or holes, therefore it would not be possible on a channel highly interconnected with pores in a porous biomaterial.

Applicant has also noticed that the most popular current solutions for breast reconstruction can only fill volume deficit after trauma or tumor resection and are not able to effectively:
i) promote the rapid vascularization in vitro and in vivo,
ii) allow a natural and permanent regeneration of large tissue volume, and
iii) restore both function and volume of adipose tissue.

DISCLOSURE OF THE INVENTION

The object of the present invention is thus to meet the needs outlined above.

According to the present invention, such an object is achieved by means of a biodegradable medical device for breast reconstruction and augmentation having the features set forth in the claims that follow.

The following summary of the invention is provided in order to provide a basic understanding of some aspects and features of the invention. This summary is not an extensive overview of the invention, and as such it is not intended to particularly identify key or critical elements of the invention, or to delineate the scope of the invention. Its sole purpose is to present some concepts of the invention in a simplified form as a prelude to the more detailed description that is presented below.

According to a feature of a preferred embodiment according to present invention, the biodegradable medical device is made of a polymeric matrix having a particular internal morphology characterized by an open-pore structure.

According to a further feature of the present invention, the polymeric matrix constituting said medical device is a bio-resorbable porous polymeric matrix composed of a tailor-made poly(urea-urethane-ester-ether) "PUUEE" soft foam, which is particularly indicated for the clinical application of the medical device according to the present invention.

According to another feature of present invention, the PUUEE soft foam may also contain medium molecular weight hydrophilic polyalkoxide polyols, as for example, polyethylene glycol (PEG) and/or polypropylene oxide (PPO).

According to a further feature of present invention the medical device comprises channels which propagate three-dimensionally, according to well-defined patterns and geometries, through the interconnected open-pore structured polymeric matrix.

Thanks to its particular open-pore structure and the presence of channels which propagates in the porous structure, the medical device of this invention possesses an high interconnected architecture, obtained by a simple and scalable process. This particular architecture can be used to promote rapid and efficient cell penetration and blood vessel formation through the inner parts of said medical device.

According to another feature of present invention, the channelization of said porous polymeric matrix is achieved according to an innovative technique, called "thermal drilling". The technique is based on the perforation of polymeric porous matrixes by means of heated tools that are arranged for penetrating the porous matrixes and to perform a permanent and pre-defined channelization, thanks to their high temperatures.

BRIEF DESCRIPTION OF DRAWINGS

These and further features and advantages of the present invention will appear more clearly from the following detailed description of preferred embodiments, provided by way of non-limiting examples, with reference to the attached drawings, in which components designated by same or similar reference numerals indicate components having same or similar functionality and construction and wherein.

BEST MODES FOR CARRYING OUT THE INVENTION

Figure 1:
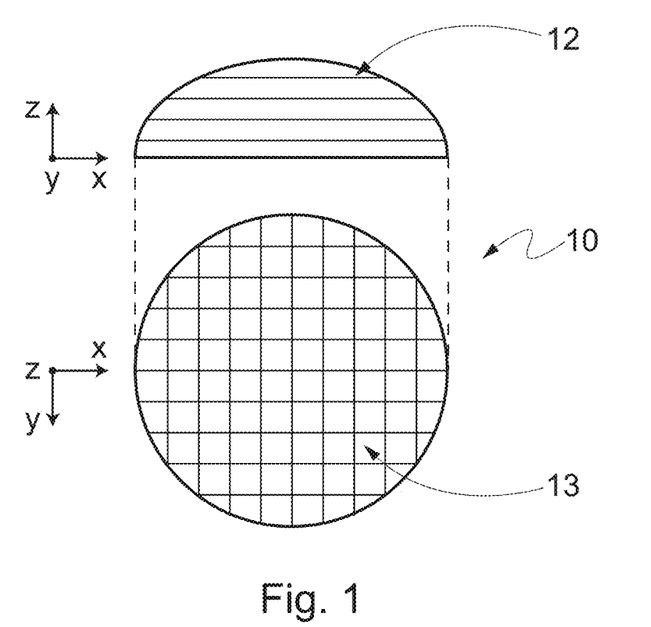
FIG. 1 shows a schematization of a spherical cap-shaped medical device according to present invention, with 4 grid-shaped channel networks positioned at different levels along the Z-axis; front view (FIG. 1a) and view from above (FIG. 1b)
Figure 2:
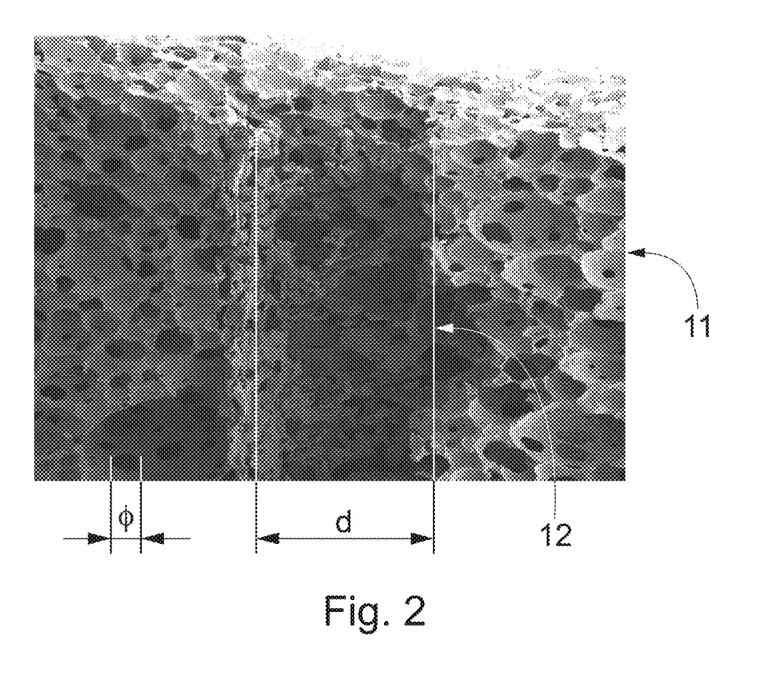
FIG. 2 shows a SEM micrograph of a PUUEE-based polymeric matrix, channelized according to thermal drilling technique.

With reference to FIGS. 1 and 2, the medical device according to a first embodiment of the present invention is, for example, a spherical cap-shaped scaffold 10.

The scaffold is preferably made of a soft polymeric matrix having a porous structure 11 (i.e. a soft polymeric foam) and belonging, preferably, to the family of poly(urea-urethane)s. More preferably, the polymeric matrix belongs to poly(urea-urethane-ester-ether)s, called "PUUEE".

The PUUEE-based polymeric matrix is composed by a reactive mixture comprising:

1) at least 30% (w/w) high-to-medium molecular weight hydrophobic biodegradable amorphous soft segments polyols, of average molecular weight from 20'000 to 60'000 Da. In particular, the hydrophobic biodegradable amorphous soft segments polyols, constituting at least 30% (w/w) of PUUEE, must contain at least 10% (w/w) 1,4-Dioxane-2,5-dione (commonly named glycolide) and at least 40% (w/w) 2-oxepanone (commonly named epsilon-caprolactone).

Moreover, the number of reactive terminal hydroxide groups of said hydrophobic biodegradable amorphous soft segments polyols are ranged between 6 to 2 per macromolecule, more preferably between 4 to 2 per macromolecule.

2) medium molecular weight hydrophilic polyalkoxide polyols, of average molecular weight from 2'000 to 15'000 Da, as for example, polyethylene glycol (PEG), polypropylene oxide (PPO), random copolymers of ethylene glycole and propylene oxide (P(ED-co-PO).

In particular, the number of reactive terminal hydroxide groups of said hydrophilic polyalkoxide polyols are ranged between 4 to 2 per macromolecule.

3) at least 40% (w/w) low molecular weight polyisocyanates and polyols, whose average molecular weights range between 15 and 200 Da.

The weight ratio between the hydrophobic biodegradable soft segment polyols and the hydrophilic polyalkoxide polyols is comprised between 10:1 to 1:1, more preferably between 5:1 and 2:1, and most preferably between 4:1 and 3:1.

The percentage of isocyanate functional groups involved in the syntheses of PUUEE soft foams and chemically convertible to urea groups (hard segments) ranges preferably between 50 and 65% of the total amount of isocyanate groups, more preferably between 60 and 63%.

In addition, the urea content in the PUUEE foam preferably must not exceed 65.5% of the total convertible isocyanate groups.

The PUUEE foam according to the present invention is a flexible foam characterized by low cross-linking degrees.

This is due to its particular macromolecular structural design, mainly based on:
i) the introduction and copolymerization of high-to-medium molecular weight amorphous soft segments
ii) low polyurea hard segments content, and
iii) as low as possible cross-linking degree, in order to avoid foam rigidity.

The copolymerization of high-to-medium molecular weight amorphous soft segments (at least 30% (w/w)), whose average molecular weights are higher than 20'000 Da, is such to make possible to finely tune the visco-elastic properties of the foam and to obtain flexible foams, which are characterized by low cross-linking degrees.

According to a further characteristic of the present invention, the soft polymeric matrix preferably comprises a plurality of through-channels (channels) 12, which propagate in the polymeric matrix and are interconnected with its porous structure. Preferably the channels are evenly spaced within the matrix; For instance, they are placed at a substantially regular distance from each other along the X, Y, and Z-axis.

According to one embodiment of the present invention, the channels are arranged in grid-shaped networks 13 positioned at different levels along a Z-axis.

Figure 3:
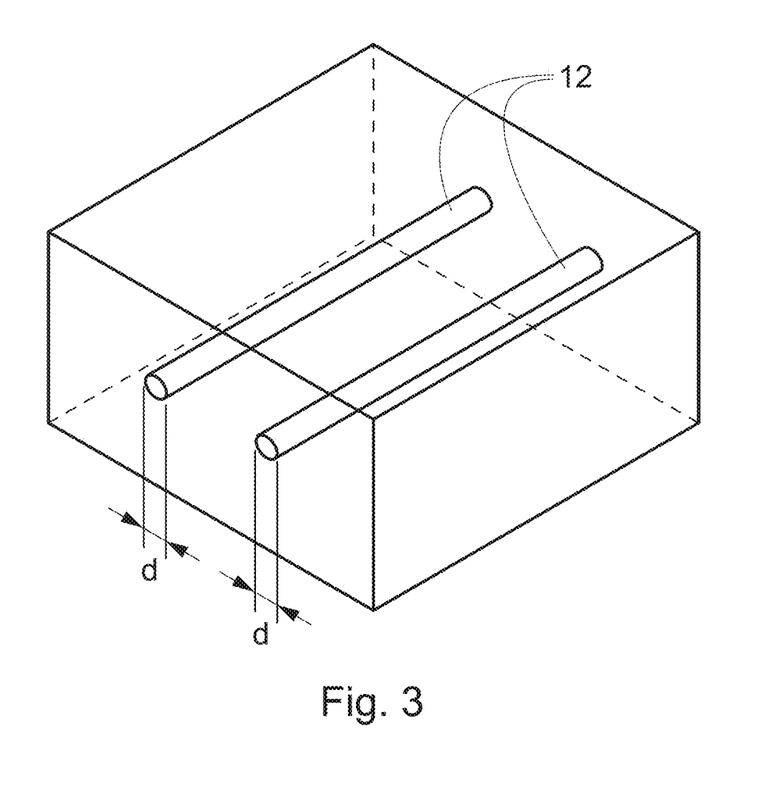
FIG. 3 shows a schematization of rectilinear, cylindrical channels embedded in a parallelepiped-shaped solid matrix and having constant diameters.
Figure 4:
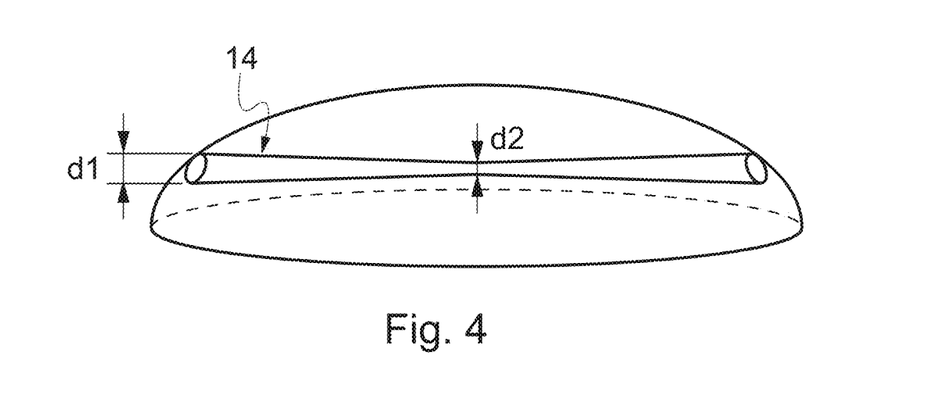
FIG. 4 shows a schematization of a through-channel in a spherical cap-shaped scaffold with a variable diameter.

According to such embodiment of the present invention, the channels 12 have constant diameters d along their length (FIG. 3). According to other embodiments, the channels 14 may have variable diameters, for example a larger diameter d1 at the scaffold surface and a smaller diameter d2 inside the scaffold (FIG. 4).

The physico-chemical properties of the medical device, in particular porosity degree (defined as the ratio between volume of pores and total volume), pore size, channels diameters, mechanical properties (Compressive Elastic Modulus), water uptake capacity (as defined in Example 2) and degradation kinetics in vitro, are listed in Table 1, providing, for each of these parameters, a preferable, more preferable and most preferable range of values.

TABLE 1

| Parameter | Value interval | More preferable value interval | Most preferable value interval |
|---|---|---|---|
| Porosity degree (%) | 55-98 | 70-95 | 80-90 |
| Pore size (diameter φ; μm) | 5-2000 | 15-1000 | 50-500 |
| Channles (diameter d; mm) | 0.50-10 | 0.3-5 | 0.8-2 |
| Mechanical properties (Compressive Elastic Modulus; kPa) | 5-700 | 5-50 | 10-30 |
| water uptake capacity (w/w; %) | 20-500 | 50-400 | 200-350 |
| degradation kinetics in vivo (months) | 1-24 | 2-12 | 2-6 |

According to other embodiments of the present invention, the scaffold can have different sizes and shapes, which depend on the breast volume deficit after tumor resection.

Also, alternative embodiments with different arrangements of the channels inside the scaffold are possible, provided that the channels are placed at a substantially regular distance along the X, Y, and Z-axis. Indeed, such an arrangement is able to promote cell penetration and homogeneous perfusion of nutrient and oxygen inside the scaffold, vascularization and tissue regeneration.

Figure 5:
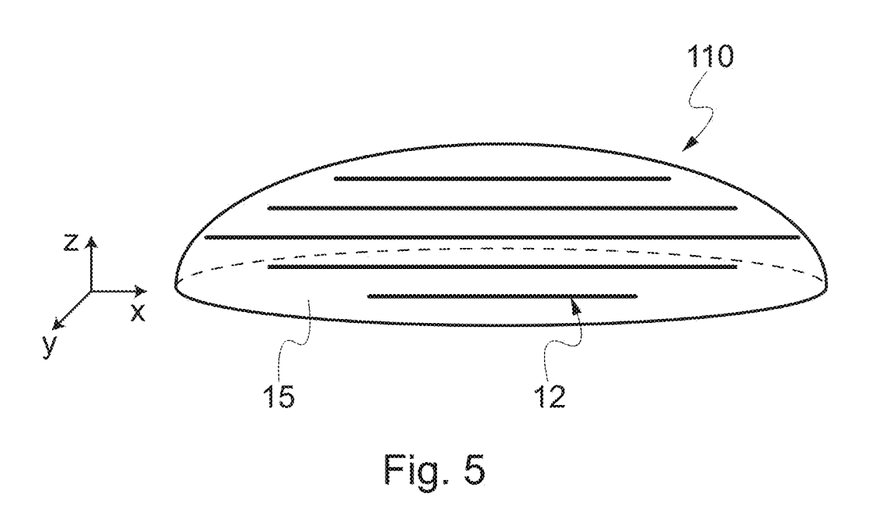
FIG. 5 shows a schematization of a spherical cap-shaped scaffold with through-channels parallel to the X-axis.

According to a first of these alternative embodiments, the medical device is a spherical cup-shaped scaffold 110 with through-channels 12 parallel to the base 15 of the spherical cup, for example parallel to the X-axis, as in FIG. 5.

Figure 6:
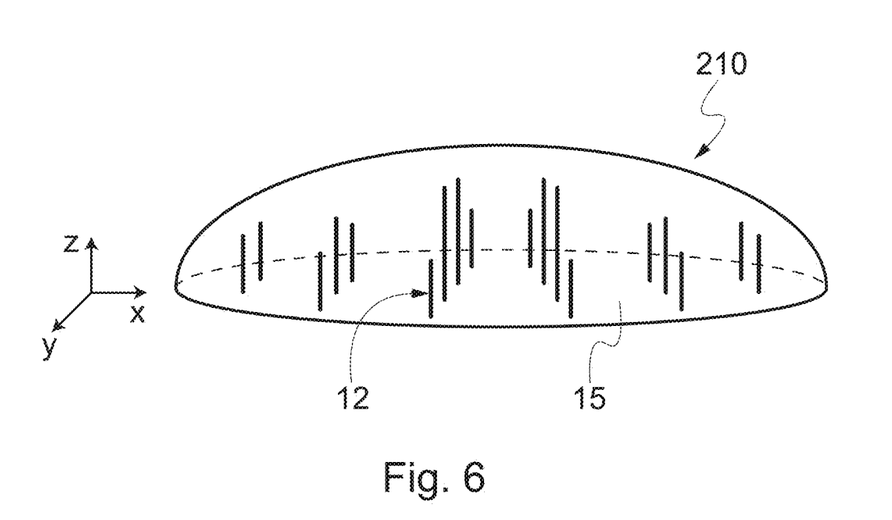
FIG. 6 shows a schematization of a spherical cap-shaped scaffold with through-channels parallel to the Z-axis.

According to a second alternative embodiment, the medical device is a spherical cap-shaped scaffold 210 with through-channels 12 perpendicular to the base 15 of the spherical cup, i.e. parallel to the Z-axis (FIG. 6).

Figure 7:
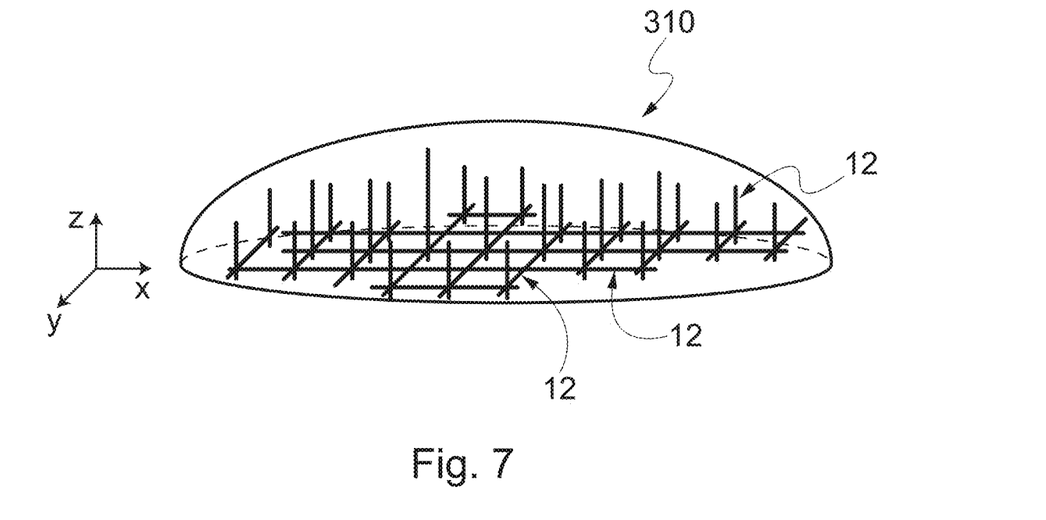
FIG. 7 shows a schematization of a spherical cap-shaped scaffold with through-channels parallel to the Y, X and Z-axis.

According to a third alternative embodiment, the medical device is a spherical cup-shaped scaffold 310 with through-channels 12 parallel to the X, Y and Z-axis (FIG. 7).

Figure 8:
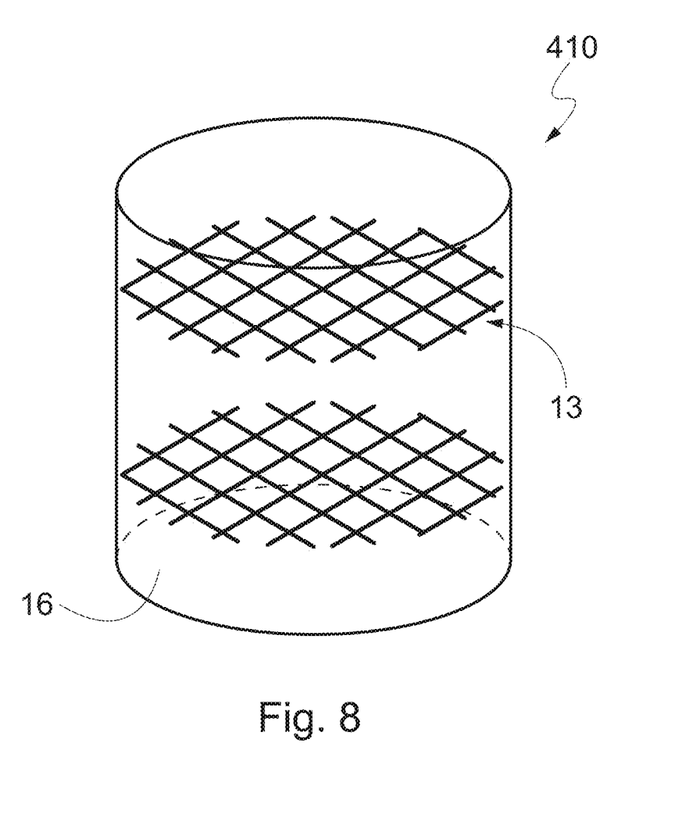
FIG. 8 shows a schematization of a cylinder-shaped scaffold with two different grid-shaped channel networks at two different levels along the Z-axis.

According to a fourth alternative embodiment, the medical device is a cylindrical scaffold 410 with at least one grid-shaped channel network 13 parallel to the base 16 of the cylindrical scaffold, i.e. to the X-Y plane. For example, the scaffold 410 has two grid-shaped channel networks 13, as shown in FIG. 8.

Figure 9:
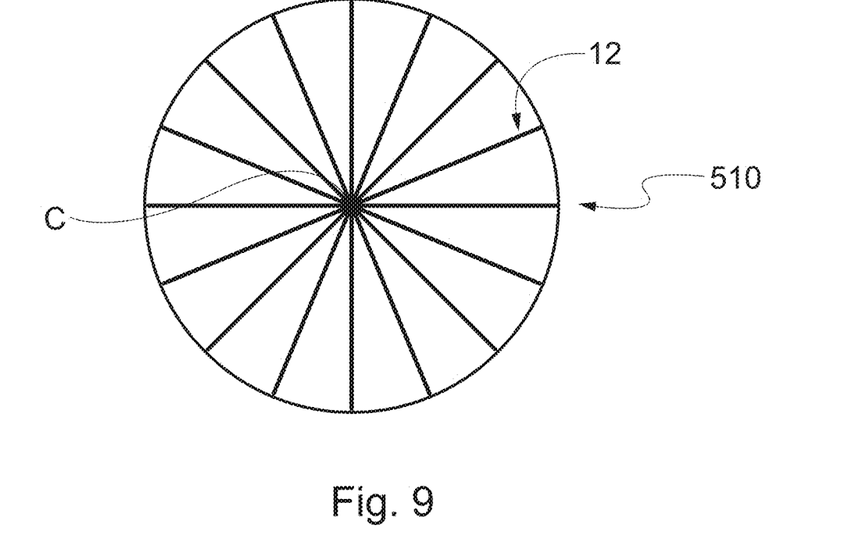
FIG. 9 shows a schematization of a spherical cap-shaped scaffold with concentric through-channels.

According to a fifth alternative embodiment, the medical device is a spherical cup-shaped scaffold 510 with radial through channels 12 intersecting in a common point C (FIG. 9).

Figure 10:
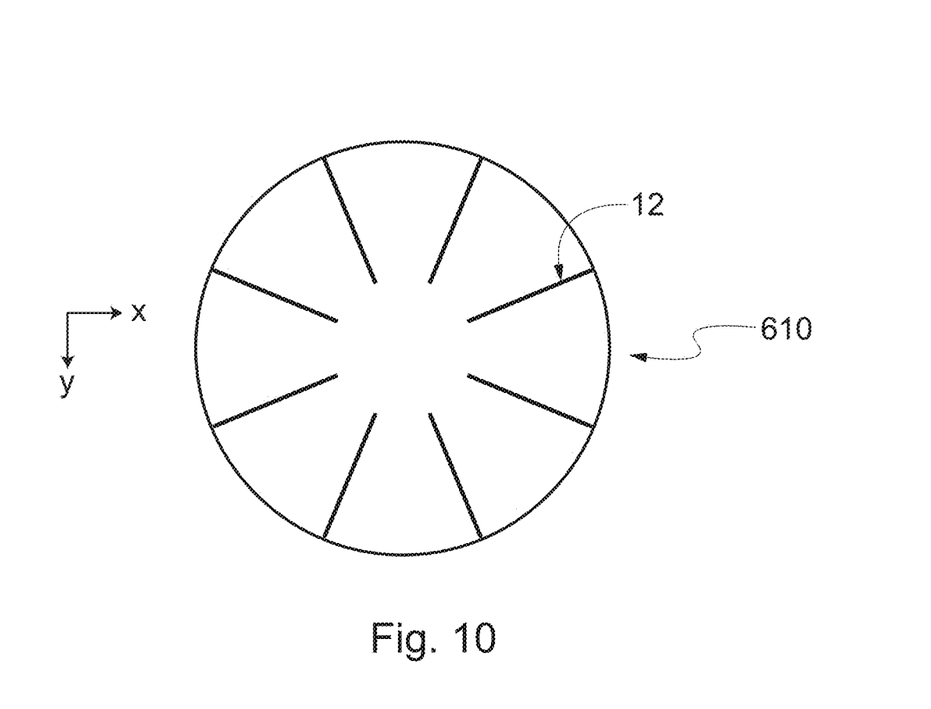
FIG. 10 shows a schematization of a spherical cap-shaped scaffold with concentric dead-end channels.

According to a sixth alternative embodiment, the medical device is a spherical cup-shaped scaffold 610 with radial dead-end channels 12 (FIG. 10).

Figure 11:
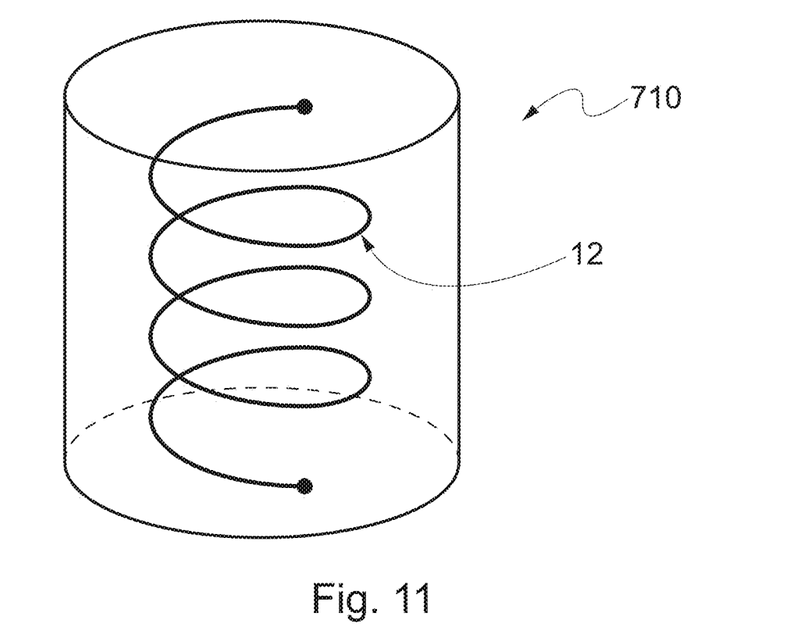
FIG. 11 shows a schematization of a cylinder-shaped scaffold with a spiral-shaped channel.

According to a seventh alternative embodiment, the medical device is a cylindrical scaffold 710 with at least one spiral-shaped channel 12 (FIG. 11).

The invention is further illustrated by means of the following examples of a method for producing and characterizing the medical device as disclosed above.

EXAMPLES

Example 1: Synthesis of PUUEE Foam

Polyol solution are prepared by mixing the following ingredients as indicated in table 2a, 2b and 2c. Hardener/catalyst solution is prepared as indicated in table 3a, 3b and 3c.

The polyol and hardener solution are mixed, by means of mechanical stirring at 400-600 rpm, from one to two minutes and let to expand freely for another minute, before solidification.

According to this procedure, the average pore size of the foam is inversely proportional to stirring time, before cross-linking. The longer the time of mechanical stirring the smaller the pore size. Temperature can accelerate the reaction kinetics, and can be applied to shorten cross-linking time intervals. However according to this casting strategy, which is "one shot", the exothermic process characterizing the poly addition reaction between the low molecular weight molecules, involved in the formulation, is sufficient to push the conversion degree of the starting materials up to 100%.

TABLE 2a

| Ingredient | Part per hundred pph (w/w) |
|---|---|
| Polyester triol, average number molecular weight 21000 Da | 30 |
| Polyethylene glycole, average number molecular weight 6000 Da | 10 |
| Glycerol | 10 |
| Distilled water | 3 |
| Dimethyl sulfoxide (DMSO) | 44 |
| Calcium stearate | 3 |

TABLE 2b

| Ingredient | Part per hundred pph (w/w) |
| --- | --- |
| Polyester triol, average number molecular weight 24000 Da | 40 |
| Polyethylene glycole, average number molecular weight 6000 Da | 10 |
| Glycerol | 10 |
| Distilled water | 3 |
| Dimethyl sulfoxide (DMSO) | 34 |
| Calcium stearate | 3 |

TABLE 2c

| Ingredient | Part per hundred pph (w/w) |
| --- | --- |
| Polyester triol, average number molecular weight 21000 Da | 30 |
| Polyethylene glycole, average number molecular weight 4000 Da | 11 |
| Glycerol | 9 |
| Distilled water | 3 |
| Dimethyl sulfoxide (DMSO) | 44 |
| Calcium stearate | 3 |

TABLE 3a

| Ingredient | Part per hundred pph (w/w) |
| --- | --- |
| tetramethylenediisocyanate | 70 |
| Ferric acetylacetonate | 0.1 |
| Dimethyl sulfoxide (DMSO) | 30 |

TABLE 3b

| Ingredient | Part per hundred pph (w/w) |
| --- | --- |
| Isophoronediisocyanate | 85 |
| Ferric acetylaceonate | 0.1 |
| Dimethyl sulfoxide (DMSO) | 15 |

TABLE 3c

| Ingredient | Part per hundred pph (w/w) |
| --- | --- |
| Hexamethylenediisocyanate | 80 |
| Ferric acetylacetonate | 0.1 |
| Dimethyl sulfoxide (DMSO) | 20 |

The physico-chemical properties of PUUEE foams obtained according to Example 1 (in particular porosity degree, pore size, mechanical properties, water uptake capacity and degradation kinetics in vitro) conform to those listed in Table 1, in the column "Most preferable value interval".

It is possible to further tune the most of the previously mentioned physico-chemical properties, in particular, mechanical properties, water uptake capacity and degradation kinetics in vitro, by changing the average molecular weight of the amorphous soft segments and the weight ratio between the hydrophilic and the hydrophobic biodegradable segments, copolymerized in the polymeric matrixes.

Moreover, in the hardener/catalyst solution, the DMSO solvent can be replaced by any other organic solvent having equivalent characteristics to DMSO.

Example 2: Shaping and Channelization of PUUEE Foam

A PUUEE foam with cylindrical shape is synthesized according to example 1.

A hot wire is used to cut the external part of the cylinder, in order to obtain a semi-spherical caps.

Once the foam has been shaped externally, a network of channels is realized inside the foam by perforating the foam with a series of hot needles. The needles are heated, electrically, at temperatures range 100-200° C., preferably between 130 and 170° C.

The needles are inserted through the foam's matrix and retracted after a time interval ranging from 1 second and 20 seconds, preferably between 5 and 10 seconds.

The diameter of the needle ranges 0.1 mm to 5 mm, preferably between 0.5 and 2 mm. The diameter of the resulting channels depends on both the diameter of the tool and its permanence time inside the foam, where higher permanence times produce larger channels.

The network of channels is produced by perforating the foam in different areas of the spherical cap and in different directions, according to well-defined 3 dimensional pattern. In this example, the network of channels is obtained by:

(1) producing parallel channels which lie in the same horizontal plane, arranged at 5 mm one from each other (X-axis);
(2) producing parallel channels, arranged at 5 mm one from each other, orthogonal to and lying in the same plane of those one produced in the step 1 (Y-axis);
(3) reproducing the same channels produced in steps 1 and 2 in different planes, at 5 mm distance one from each other;
(4) producing channels orthogonal to those produced in steps 1 and 2, arranged at 5 mm one from each other (Z-axis).

At the end of the process, a spherical cap-shaped foam with an internal three-dimensional network of channels, at a maximum distance of 5 mm one from each other, is obtained.

Example 3: Chemical and Physical Characterization of PUUEE Prosthesis

Uniaxial compression test: six cylindrical specimens, of 1 cm diameter and 1 cm height were used to determine the elastic compressive modulus and compressive strength of the prosthesis.

All measurements were carried out at room temperature (25° C.) on swollen samples in distilled water. The samples were compressed at the speed of 1 mm/min.

Compressive elastic modulus was calculated by the slope of stress-strain curve at the deformation zone between 5 and 10%.

Compressive strength was calculated as the maximum stress at deformation higher than 95%.

Figure 13:
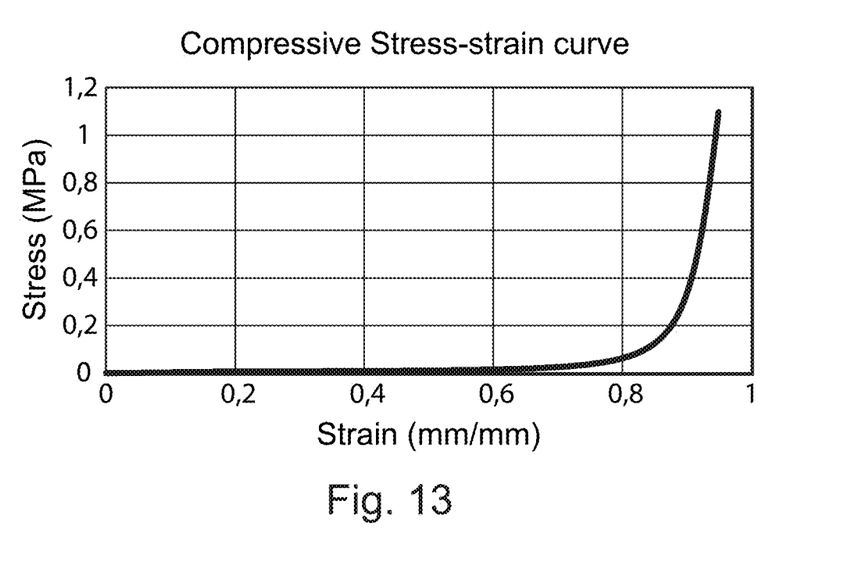
FIG. 13 shows the compression stress-strain curve of PUUEE-based prosthesis, synthesized according to Example 1 of the present invention.

The stress strain curve of the prosthesis obtained according to Example 1 is illustrated in FIG. 13.

The prosthesis are characterized by a 30 kPa compressive elastic modulus and a compressive strength (at 95% deformation) of 1 MPa.

Weight Water uptake tests: six purified and dried cylindrical samples were incubated in phosphate buffer saline solution (PBS 1×). At each time point, the swollen samples were removed from PBS, blotted gently to remove excess PBS.

Figure 14:
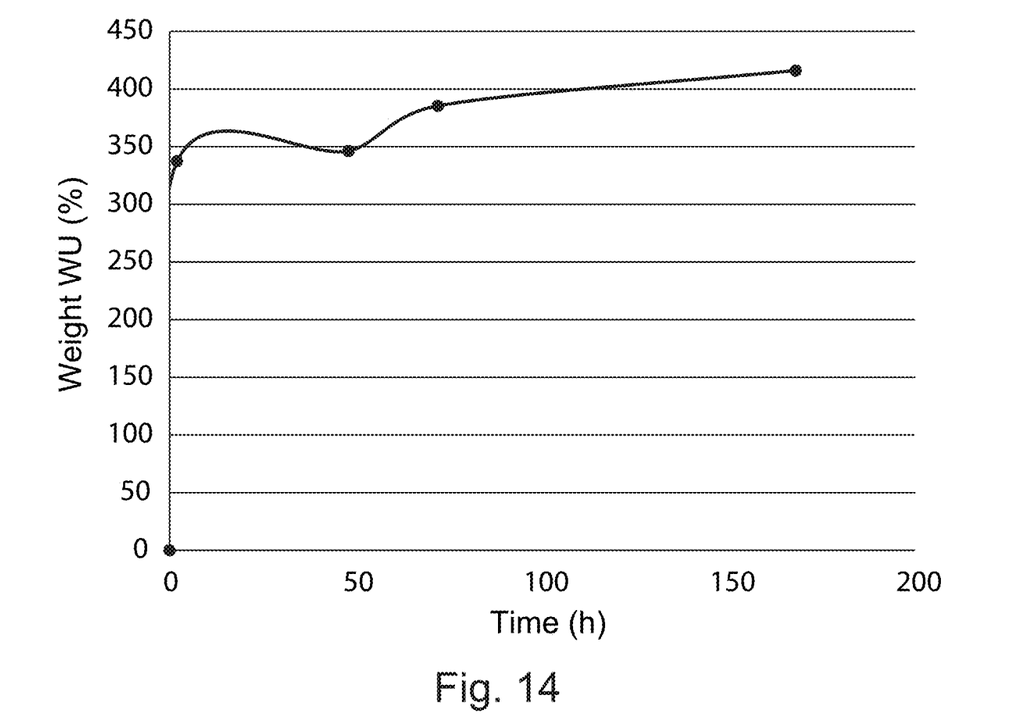
FIG. 14 shows the weight water-uptake kinetics of PUUEE-based prosthesis, synthesized according to Example 1 of the present invention.

The Weight Water uptake curve of the prosthesis obtained according to Example 1 is shown in FIG. 14.

Weight water uptake was calculated according to the following formula:

Weight water uptake %=(Ws−W0)*100/W0

Where W0, Ws and Wd in the above equation are the initial, swollen weight respectively.

In general, according to the above examples, the method for producing the medical device according to the present invention comprises the following steps:

synthesizing the PUUEE-based polymeric matrix by mixing a solution comprising
  high-to-medium molecular weight hydrophobic biodegradable amorphous soft segments polyols of average molecular weight from 20'000 to 60'000 Da;
  medium molecular weight hydrophilic polyalkoxide polyols of average molecular weight from 2'000 to 15'000 Da;
  low molecular weight polyisocyanates and polyols of average molecular weight from 12 to 200 Da.
  according to the items 1-3 as disclosed above;
shaping the PUUEE-based polymeric matrix in order to obtain a matrix of desired shape;
realizing a plurality of channels inside the PUUEE-based polymeric matrix.

The plurality of channels are obtained by means of a versatile and scalable method, which allows the channelization of porous matrices according to well-defined three-dimensional patterns and geometries, as the ones described above.

Figure 12:
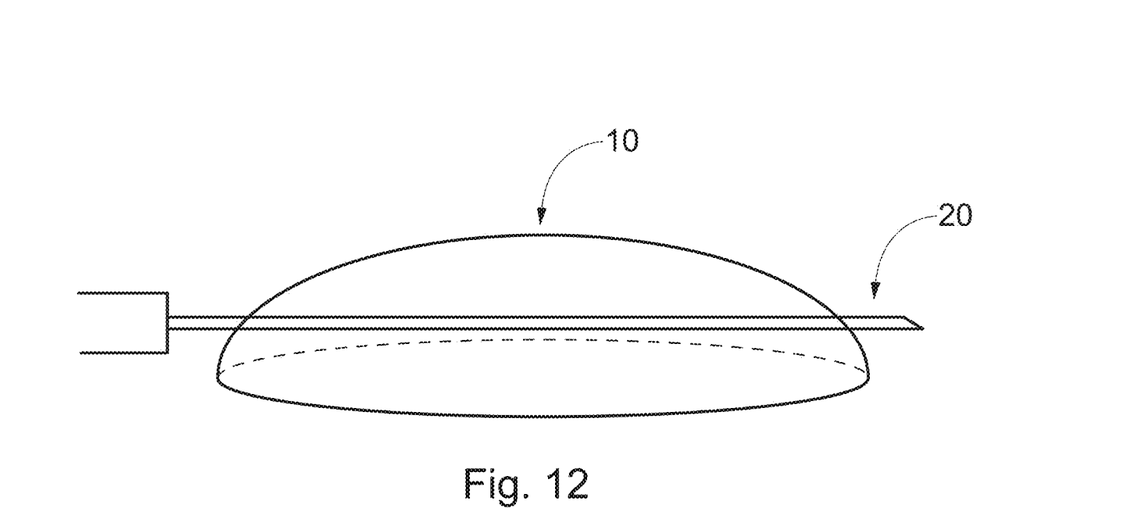
FIG. 12 shows a schematization of the thermal drilling process using a hot, rectilinear needle perforating a spherical cap-shaped scaffold.

The channelization technique is based on thermal drilling, i.e. on the perforation of the porous polymeric matrix by means of a heated tool 20 (FIG. 12), which is able to easily penetrate the matrix causing permanent modification of the internal morphology in those areas of the polymeric porous matrices which come in contact with the tool.

For example, the perforating tool is shaped as a series of needles, mandrels or metallic sticks, whose cross-section is, for example, circular, squared or with other design and whose geometry is rectilinear or curved.

The temperature of the perforating tool ranges preferably from 30° C. to 400° C., more preferably between 100° C. and 200° C., and most preferably between 130° C. and 170° C.

Thanks to the high temperature of the perforating tool, the parts of polymeric matrix which come in contact with the heated tool is subjected to thermal decomposition, and this consequently leads to permanent modification of the internal morphology of the polymeric matrix. This technique is also applicable to porous scaffolds based on synthetic polymers such as polyurethanes, polyacrylates, polyesters, polyamides, vinylic polymers, polyanhydrides, polyolefines, silicones, their copolymers and mixtures, and natural origin polymers such as collagene, gelatin, hyaluronic acid, polylysine, laminin, fibronectin and their copolymers and mixtures.

The channelization technique of the present invention is also suitable for stiff, porous polymeric matrixes, as the heated tool, being made of a metal alloy, is able to penetrate and shape stiff polymers, even in presence of inorganic fillers such as hydroxyapatite.

The particular internal morphology of the medical device according to the present invention resembles, advantageously, the architecture of the natural biological tissues and is suitable to promote the recruitments of blood vessels (vascularization) and soft tissue restoration (instead of simply replacing the removed soft tissue).

Indeed, the tailor-made synthetic polymer of the medical device according to the present invention has adequate mechanical properties (such as good elasticity, hardness, shape memory), hydrophilic character and degradation kinetics suitable for the adipose tissue regeneration in vivo.

Furthermore, the particular architecture of the medical device of the present invention is obtained by means of a simple and scalable process.

The casting strategy used for obtaining the soft PUUEE foam is a "one shot" casting strategy, which advantageously lead to cross-linked soft polyurethane foams. This is achieved thanks to the characteristic high exothermic process, resulting from the poly addition reaction of low-molecular weight polyols and polyisocyanates. The heat produced during the polymerization of low-molecular weight monomers contributes, advantageously, to the enhancement of the miscibility and reactivity of the high-to-medium molecular weight soft segments, which are necessary to obtain soft foams.

In addition to the casting strategy, the characteristic softness of the PUUEE foam is obtained thanks also to a well-defined urea content (hard segments), which, according to the present invention, does not exceed 65.5% of the total convertible isocyanate groups.

Furthermore, the channelization technique according to the present invention is able to re-model the porous matrix around the heated needles or mandrels. When the technique is used with the polyurethane of the present invention or with other synthetic polymers such as the ones listed above, this result is achieved without creating neither toxic nor dangerous by-product, such as oxidized substances or combustion residues, at measurable concentration, as experimentally demonstrated by the Applicant by thorough cytotoxicity Finally, despite the medical device of the present invention in particularly suitable for breast reconstruction or augmentation, it can be used, in general, for adipose tissue reconstruction, and, more in general, for soft tissue reconstruction.

Of course, without prejudice to the basic principles of the invention, the details and embodiments may vary, also significantly, with respect to what has been described herein by way of example only, without departing from the scope of the invention as defined by the claims that follow.

The invention claimed is:

1. An implantable biodegradable medical device arranged for breast reconstruction and/or augmentation, said device being made of an interconnected porous structured polymeric matrix and belonging to the family of poly(urea urethane)s, comprising:
  said polymeric matrix comprises a plurality of three dimensional channels three dimensionally propagating through the polymeric matrix and interconnected with the porous structure of said polymeric matrix, wherein said polymeric matrix comprises
    high to-medium molecular weight hydrophobic biodegradable amorphous soft segments polyols having average molecular weight comprised between 20,000 and 60,000 Da;
    hydrophilic polyalkoxide polyols, of average molecular weight comprised between 2,000 and 15,000 Da;

low molecular weight polyisocyanates and polyols, whose average molecular weights range between 15 and 200 Da.

2. The medical device according to claim 1, wherein said channels are evenly spaced within the matrix and have a distance each other smaller than 5 mm.

3. The medical device according to claim 1, wherein said channels have diameters (d) of between 0.05 and 10 mm.

4. The medical device according to claim 1, wherein said hydrophobic biodegradable amorphous soft segments polyols
   are at least 30% of the total weight of the polymeric matrix;
   contain at least 10% (w/w) 1,4 Dioxane 2,5 dione (commonly named glycolide) and at least 40% (w/w) 2-oxepanone (commonly named epsilon-caprolactone);
   comprise a number of reactive terminal hydroxide groups which ranges between 6 and 2 per macromolecule.

5. The medical device according claim 1, wherein said hydrophilic polyalkoxide polyols comprise a number of reactive terminal hydroxide groups which ranges between 4 to 2 per macromolecule.

6. The medical device according to claim 1, wherein a weight ratio comprised between 10:1 to 1:1 is provided between the hydrophobic soft segment polyols and the hydrophilic polyalkoxide polyols.

7. The medical device according to claim 1, wherein said low molecular weight polyisocyanates and polyols are at least 40% of the total weight of the polymeric matrix.

8. The medical device according to claim 1, wherein the polymeric matrix comprises a certain content of urea groups derived from isocyanate groups convertible to urea groups, said certain content not exceeding 65.5% of said isocyanate groups convertible to urea groups.

9. A method for producing an implantable biodegradable medical device for breast reconstruction and/or augmentation, said method comprising the steps of
   synthesizing a PUUEE-based polymeric matrix having a soft porous structure by mixing a solution comprising
      high-to-medium molecular weight hydrophobic biodegradable amorphous soft segments polyols of average molecular weight from 20,000 to 60,000 Da,
      medium molecular weight hydrophilic polyalkoxide polyols of average molecular weight from 2,000 to 15,000 Da,
      low molecular weight polyisocyanates and polyols of average molecular weight from 15 to 200 Da,
   shaping the PUUEE-based polymeric matrix in order to obtain a matrix of desired shape.
   drilling, by means of heated tools, a plurality of channels three dimensionally propagating through the PUUEE based polymeric matrix and interconnected with the porous structured of the PUUEE-based polymeric matrix.

10. The method according to claim 9, wherein said hydrophobic biodegradable amorphous soft segments polyols
    are at least 30% of the total weight of the polymeric matrix;
    contain at least 10% (w/w) 1,4 Dioxane 2,5 dione (commonly named glycolide) and at least 40% (w/w) 2-oxepanone (commonly named epsilon-caprolactone);
    comprise a number of reactive terminal hydroxide groups which ranges between 6 and 2 per macromolecule.

11. The method according to claim 9, wherein said hydrophilic polyalkoxide polyols comprise a number of reactive terminal hydroxide groups which ranges between 4 to 2 per macromolecule.

12. The method according to claim 9, wherein a weight ratio comprised between 10:1 to 1:1 is provided between the hydrophobic soft segment polyols and the hydrophilic polyalkoxide polyols.

13. The method according to claim 9, wherein said low molecular weight polyisocyanates and polyols are at least 40% of the total weight of the polymeric matrix.

14. The method according to claim 9, wherein the polymer matrix comprises a certain content of urea groups derived from isocyanate groups convertible to urea groups, said certain content not exceeding 65.5% of said isocyanate groups convertible to urea groups.

15. The method according to claim 9, wherein said matrix has a compressive elastic modulus between 5 and 700 kPa and wherein said porous structure comprises pores having sizes (d) of between 5 and 2000 μm.

16. The medical device according to claim 2, wherein said channels have diameters (d) of between 0.05 and 10 mm.

* * * * *